(12) United States Patent
Koest (10) Patent No.: US 7,575,323 B2
(45) Date of Patent: Aug. 18, 2009

(54) METHOD AND DEVICE FOR DETERMINING THE DISTANCE FROM A MEASUREMENT POINT ON A TISSUE SURFACE OF THE EYE

(75) Inventor: Gert Koest, Hannover (DE)

(73) Assignee: Oculus Optikgeraete GmbH, Wetzlar Dutenhofen (DE)

( * ) Notice: Subject to any disclaimer, the term of this patent is extended or adjusted under 35 U.S.C. 154(b) by 426 days.

(21) Appl. No.: 11/638,247

(22) Filed: Dec. 12, 2006

(65) Prior Publication Data
US 2007/0188708 A1  Aug. 16, 2007

(30) Foreign Application Priority Data
Dec. 13, 2005  (DE) .................. 10 2005 059 923

(51) Int. Cl.
*A61B 3/00* (2006.01)
*A61B 3/10* (2006.01)
(52) U.S. Cl. ..................... 351/246; 351/205
(58) Field of Classification Search ................ 351/246, 351/200, 208, 205–206, 210, 221
See application file for complete search history.

(56) References Cited

U.S. PATENT DOCUMENTS

| | | | |
|---|---|---|---|
| 4,261,367 A | | 4/1981 | Freese |
| 4,666,269 A | * | 5/1987 | Nakamura et al. .......... 351/212 |
| 4,738,529 A | | 4/1988 | Hug |
| 5,280,313 A | * | 1/1994 | Kohayakawa ............... 351/211 |
| 5,347,328 A | | 9/1994 | Sekine et al. |

(Continued)

FOREIGN PATENT DOCUMENTS

DE  33 24 341 A1  1/1985

(Continued)

OTHER PUBLICATIONS

European Patent Office Search Report for EP Counterpart Patent No. 06023207.1 (Oct. 17, 2008).

*Primary Examiner*—Scott J Sugarman
*Assistant Examiner*—Dawayne A Pinkney
(74) *Attorney, Agent, or Firm*—Blakely, Sokoloff, Taylor & Zafman LLP (57) ABSTRACT

The invention relates to a method and a device for determining the distance from a measurement point on a tissue surface (10, 13) of the eye (02), wherein
a) an initial light pulse (09*a*) is generated using a pulse light source (03) and is directed onto the measurement point of the eye,
b) a reflector light pulse (11) reflected on the tissue surface (10, 13) at the measurement point is intercepted by a light sensor (04),
c) a follow-up light pulse (09*b*) of the pulsed light source (03) is triggered by the detection of the reflector light pulse (11) at the light sensor (04),
d) the pulsed light source (03) generates further follow-up light pulses (09*b*) depending on the detection of the reflector light pulses (11) caused by the respectively preceding follow-up light pulses (09*b*) and thereby oscillates at a frequency F1,
e) the frequency F1 is measured directly or indirectly,
f) the length X of the ray path starting from the pulsed light source (03) via the measurement point to the light sensor (04) is derived from the measured value F1 and the specific speed of light c at which the light propagates in the medium along the ray path.

53 Claims, 10 Drawing Sheets

U.S. PATENT DOCUMENTS

| | | |
|---|---|---|
| 6,053,613 A | 4/2000 | Wei et al. |
| 6,231,186 B1 | 5/2001 | Broadus et al. |
| 6,806,963 B1 | 10/2004 | Walti et al. |
| 2003/0072007 A1 | 4/2003 | Fercher |

FOREIGN PATENT DOCUMENTS

| | | |
|---|---|---|
| DE | 34 29 062 A1 | 2/1986 |
| WO | WO 2005/058152 A1 | 6/2005 |

* cited by examiner

METHOD AND DEVICE FOR DETERMINING THE DISTANCE FROM A MEASUREMENT POINT ON A TISSUE SURFACE OF THE EYE

FIELD

The invention relates to a method and a device for determining the distance from a measurement point on a tissue surface of the eye.

BACKGROUND

Distance measurements of this type are of major importance in ophthalmology. In particular, the axial length of the eye, that is the distance between cornea and retina, is of major importance in many medical procedures. However, the measurement of the distance from measurement points on tissue surface in the interior of the eye presents considerable difficulties since the eye itself must not be injured by the measuring tools used.

The known measurement methods for measuring the eye are therefore extraordinarily expensive and inaccurate.

SUMMARY

It is therefore the object of the present invention to propose a new method for determining distances on and/or in the eye which can be carried out rapidly using relatively simple means and at the same time yields precise measurement results. It is further the object of the invention to propose a device for carrying out the method according to the invention.

These objects are achieved by a method and a device according to the teaching of the independent main claims.

Advantageous embodiments of the invention are the subject matter of the dependent claims.

The method according to the invention is based on the basic idea of using light pulses reflected from the corresponding tissue surface to measure the distance from a measurement point on a tissue surface of the eye. Since the light pulse and the light pulse reflected at the tissue surface (reflector light pulse) propagate at the speed of light, that is very rapidly, however, it is scarcely possible to directly measure the propagation time of the light from the time of emission until reception of the reflector light pulse at a light sensor. In particular, such direct measurements of the propagation time are beset with high measurement errors so that the measurement results cannot be further used in practice.

According to the invention, it is therefore proposed to construct a resonant circuit. In this resonant circuit, the respectively next light pulse of the pulsed light source (follow-up light pulse) is triggered by a reflector light pulse of the preceding follow-up light pulse being detected at the light sensor. In other words, this means that each follow-up light pulse is reflected at the tissue surface of the eye and the reflector light pulse thus produced is detected at the light sensor. The respectively next follow-up light pulse of the pulsed light source is triggered by the detection of the reflector light pulse. An initial light pulse is generated by the pulsed light source to initially set the resonant circuit in oscillation.

The frequency of the resonant circuit, that the number of follow-up light pulses per unit time, is measured directly or indirectly with suitable measuring means. In this case, the frequency measurement can be made using relatively simple measuring means.

Since the specific speed of light at which the pulsed light propagates in the medium along the ray path between the pulsed light source and the measurement point or the measurement point and the light sensor is known, the length of the ray path starting from the pulsed light source via the measurement point on the tissue surface of the eye to the light sensor can be derived from the measured oscillation frequency, from the directly or indirectly measured oscillation frequency of the resonant circuit. This is because the measured oscillation frequency contains the information as to the time required to produce the corresponding number of follow-up light pulses which have then each propagated the total length of the ray path. If this propagation time is normalised to a single follow-up light pulse and this propagation time normalised to a follow-up light pulse is multiplied by the specific speed of light, the length of the ray path is obtained.

At the same time, it is particularly preferred if the pulsed light source and light sensor are disposed in the device provided for carrying out the method in such a manner that the length X of the ray path between the pulsed light source and the measurement point precisely corresponds to the length Y of the ray path between the measurement point and the light sensor. This means in other words that the propagation time or propagation length of the follow-up light pulse starting from the pulsed light source as far as the tissue surface exactly corresponds to the propagation length or propagation time of the reflector light pulse starting from the tissue surface of the eye to the light sensor. In this way, the length of the ray path determined by evaluating the measured frequency can be simply halved to obtain in this way the sought distance between the pulsed light source and the measurement point on the tissue surface of the eye. The length of the ray path between the pulsed light source and the measurement point on the tissue surface of the eye can be calculated using the formula $X=0.5 \times c \times (1/F1)$. If the length of the ray path of the follow-up light pulse does not exactly correspond to the length of the ray path of the reflector light pulse, the factor 0.5 must be corrected by further correction factors which are added or multiplied. The factor $1/F1$ is obtained from the fact that the propagation time of the follow-up light pulse required by the follow-up light pulse starting from the pulsed light source as far as the tissue surface of the eye, is replaced by the reciprocal of the measured oscillation frequency.

Using the measurement principle according to the invention wherein measurements are made of the oscillation frequency at which the resonant circuit comprising pulsed light source, light sensor and control electronics oscillates, the respective distances from the respective tissue surfaces can be derived simply from the measured oscillation frequencies. In this case, however, it should be noted that the derived results for the length of the ray path contain a systematic measurement error caused by the delay of the signal propagation in the control electronics. After the reflector light pulse is incident at the light sensor, the light sensor requires a certain delay time dependent on the component for detecting the light signal, the control electronics requires such a delay time for transmitting the signal and the pulsed light source requires such a delay time for triggering the next follow-up light pulse. This delay time of the components used is additionally subjected to fairly large fluctuations since the components behave differently at different temperatures, for example. In order to avoid complex calibration whereby the measurement errors caused by the delay time can be eliminated or at least estimated, according to one preferred embodiment of the method it is provided that the frequency measurement is made successively during reflection of the light pulses at two different measurement points, at least one of said measurement points lying on the tissue surface of the eye.

The length difference XD by which the lengths X1 and X2 of the two ray paths differ during reflection of the light pulses at the first measurement point and during reflection of the light pulses at the second measurement point can then be derived from the two measured values F1 and F2. The length difference XD derived from the measured oscillation frequencies F1 and F2 is no longer falsified by the component-dependent delay times since this measurement error is equally large in both measured frequencies and is accordingly cancelled out when taking the difference.

If the pulsed light source and light sensor are in turn arranged in such a manner that the propagation lengths of the follow-up light pulses exactly correspond to the length of the reflector light pulses, the length difference XD can be calculated using the formula $XD=0.5 \times c \times (1/F2 - 1/F1)$.

Various alternatives exist for placement of the second measurement point for measuring the oscillation frequency F2. According to a first alternative, the second measurement point lies on a second tissue surface of the eye. In this case, the derived length difference XD represents the distance between the two tissue surfaces in the eye. The first measurement point can thus be placed, for example, on the retina of the eye and the second measurement point on the anterior side of the cornea. In this way, the axial length of the eye between cornea and retina could easily be determined from the length difference XD.

Alternatively to this, it is also feasible that the second measurement point lies on a reflecting reference surface, for example on a mirror surface arranged in the device. This has the advantage that very strong reflector light pulses are obtained when measuring the frequency F2. In addition, since the length of the ray path dependent on the component, starting from the pulsed light source via the reference surface to the light sensor is known, the measurement error caused by the component-dependent delay time can be simply eliminated by taking the corresponding length difference. In this way, the distance between the measured tissue surface and the reference point of the device is simply obtained by corresponding defined positioning of the reference surface relative to a reference point.

If a second independent measuring device, in particular a triangulation measuring device, is additionally provided in the device provided for carrying out the method, whereby the distance between a reference point in the device and a measurement point on a tissue surface on the outer side of the eye, in particular on the anterior side of the cornea, can be determined, the distance between the individual measurement points and the measurement point on the outer side of the eye can be determined by corresponding difference of the distances from the respective reference point.

The defined positioning of the difference surface for measuring the distance between different tissue surfaces in the eye can be avoided by successively making length difference measurements XD1 and XD2 in each relative to the reference surface for the various tissue surfaces. By taking the length differences XD1 and XD2, the difference between the two measurement points on the two tissue surfaces of the eye can be then be derived, the length of the ray path starting from the pulsed light source to the reference surface and to the light sensor being dropped from the calculated and thus no longer needing to be determined.

In order to be able to measure the frequency during reflection of light pulses at different tissue surfaces of the eye, the reflector light pulses reflected from the different tissue surfaces of the eye must be differentiated from one another. One possibility for differentiating the reflector light pulses at the individual tissue surfaces is to take into account the light intensity of the various reflector light pulses. This is based on the fact that a follow-up light pulse is reflected with different intensity at the various tissue surfaces of the eye, for example at the anterior side or the posterior side of the cornea or at the anterior side or posterior side of the natural lens or at the retina. The strongest reflection light pulses are obtained for reflection at the retina. Various trigger thresholds can then be defined in the measured signal spectrum of the measured light intensities. Depending on whether the individual trigger thresholds are exceeded or fallen below, the reflector light pulse of the light reflected at a particular tissue surface can then be determined from the signal received.

When selecting the various reflector light pulses of the various tissue surfaces on or in the eye, it is particularly advantageous if the light intensity of the light pulses is changed between the various measurement runs. Since various reflector light pulses are selected with a single trigger threshold, it is thereby possible that the various reflector light pulses are correspondingly attenuated or amplified in each case as a result of the attenuation or amplification of the light intensity.

The light intensity can naturally be varied by correspondingly triggering the pulsed light source with changed parameters. Since any change in the pulsed light source or the light sensor can produce changes in properties which change the component-dependent delay times, it is preferable however if the light intensity is varied by incorporating a darkening element, in particular by shifting an optical wedge element, in the ray path of the light pulses. In this way, the component-dependent delay times between the individual measurement runs always remain constant and the change in the light intensity is effected purely passively by corresponding shading with the darkening element.

The manner in which the frequency measurement is made is basically arbitrary. In particular, the frequency measurement can be made by using a time measuring device and a pulse counting device. The measurement duration of a measurement run is determined using the time measuring device whereas the pulse counting device counts the pulses delivered during the measurement duration. The respective frequency is then obtained from the relationship between the counted light pulses and the measured measurement duration.

Alternatively, it is also feasible to predefine the measurement duration of each measurement run as a fixed value and count the light pulses delivered during the measurement duration. A time measuring device for the variable time measurement can be omitted in this way.

Alternatively, it is also possible to predefine the delivered light pulses as a fixed value and measure the measurement time required to deliver this fixed number of light pulses with the time measuring device. A pulse counting member for variable counting of the delivered light pulses can be omitted in this way.

Alternatively or additionally to varying the light intensity of the light pulses delivered for reflection of the reflected reflector light pulses reflected at the various tissue surfaces, it is also feasible to provide a confocal optical filter in the ray path of the reflector light pulses. These confocal optical filters have the property that only light signals reflected in the near-field range of a particular measurement plane can pass through the optical filter. All light signals not reflected in the near-field zone of the predefined measurement plane of the optical filter are filtered out by the optical filter. The confocal filter can, for example, consist of a plurality of lenses and an aperture. By suitable focusing of the light signals in the lenses, it is achieved that only the light signals reflected at the predefined measurement plane are focused by the lenses in such a manner that they can pass through the aperture. All non-focused signals which therefore lie outside the measurement plane are filtered out by the aperture.

By means of the confocal light filter, it is thus possible that only those reflector light signals reflected in a particular measurement plane are received at the light sensor in each case. At the same time, the measurement plane of the confocal optical filter can be displaced by adjusting the optical filter. During measurements of the eye, the optical filter can then be shifted continuously or in steps in such a manner that the measurement plane is shifted from an initial position as far as an end position. The measurement plane then moves in the direction of one axis through the eye and intersections the eye at different measurement points on the tissue surfaces. As soon as a reflector light signal is detected at the light sensor, the distance measurement is made by corresponding frequency measurement. Thus, by suitably shifting the measurement plane, all tissue surfaces of the eye at which the pulsed light is reflected can be successively determined with their respective distance. For this purpose, it is particularly advantageous if the initial position or end position of the measurement plane lies before or on the anterior side of the cornea. If the initial position or end position of the measurement plane at the same time lies on or behind the retina, the entire eye can be measured as a result with the different distances between the different tissue surfaces.

Furthermore, it is particularly advantageous if the position of the eye is fixed during the frequency measurement by a fixing light source to prevent measurement errors caused by undesirable movements of the eye.

The method according to the invention can be used not only to determine distances between different tissue surfaces but also height profiles in the individual tissue surfaces.

For this purpose, the distance from a plurality of adjacent measurement points on the tissue surface of the eye is successively measured and the height profile is derived from the different measured values.

The various adjacent measurement points on the tissue surface of the eye can be measured by scanning for example. During this scanning mode the measuring beam is successively guided over the tissue surface of the eye in accordance with a predefined raster and the respective distances at the adjacent measurement points are determined. The desired height profile is then obtained from the individual measurement points.

Alternatively to using a scanning mode, a height profile can also be created by directly a plat pulsed light beam onto the tissue surface. The pulsed light beams reflected at the individual measurement points are then detected separately from one another by a flat sensor, in particular a CCD chip sensor so that the desired height profile is obtained in this way. The number of measurement runs for creating the height profile can thus be reduced considerably.

The type of height profiles measured using the method according to the invention is basically arbitrary. According to a preferred embodiment, a flat height profile of the nerve fibre head at the end of the optic nerve is derived by the method according to the invention. This height profile of the nerve fibre head can provide information on certain disease forms of the eye, in particular glaucoma.

It is furthermore particularly advantageous if the height profile of the cones on the retina is derived by the method according to the invention. In this way, any damage to the retina such as is caused by exposure to laser light, for example, can be determined.

It is fundamentally also arbitrary which tissue surfaces of the eye are determined at their distance by the method according to the invention. Particularly suitable are measurement points on the anterior side or on the posterior side of the cornea, measurement points on the anterior side or the posterior side of the natural lens and/or measurement points on the retina.

Since the speed of light differs in different types of eye tissue, these should be taken into account if possible from different propagation velocities when deriving the sought distances from the measured frequencies.

Alternatively, however, an averaged velocity can be used when calculating the derivative.

The pulsed light source should preferably be embodied in the manner of a laser light source or in the manner of a laser diode.

Photodiodes or CCD chip sensors are suitable as light sensors.

BRIEF DESCRIPTION OF THE DRAWINGS

Various embodiments are shown schematically in the drawings and explained in detail hereinafter as examples. In the figures.

DETAILED DESCRIPTION

Figure 1:
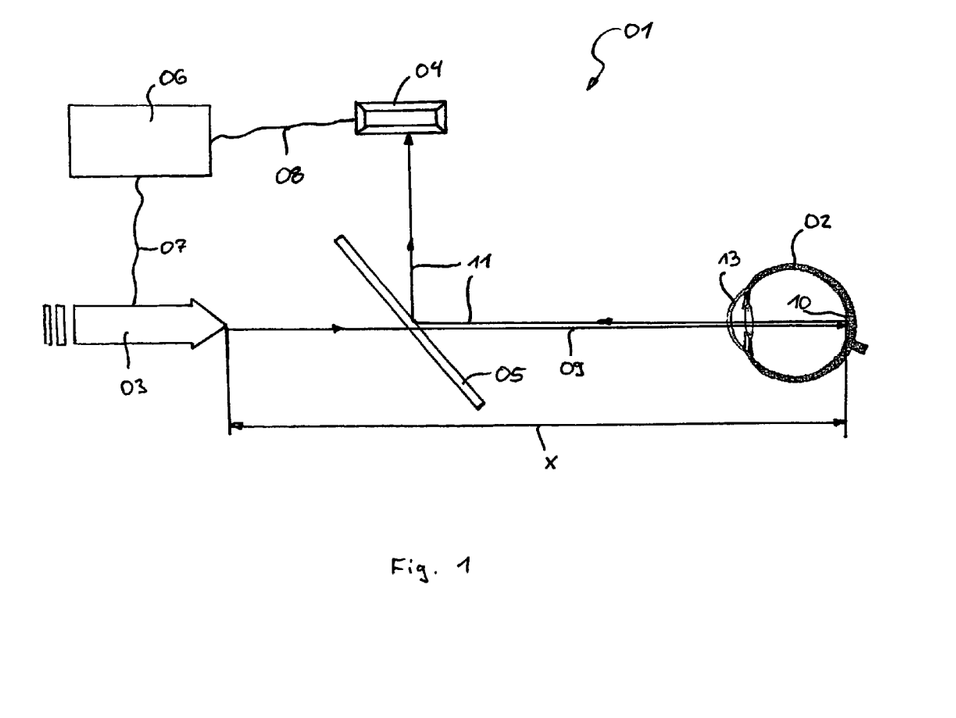
FIG. 1: shows the schematic structure of a first embodiment of a device for measuring the distance from a measurement point on a tissue surface of the eye.

FIG. 1 shows the fundamental structure of a device 01 for measuring the distance X from the eye 02. The device 01 comprises a pulsed light source 03, for example, a laser diode, a light sensor 04, for example, a photodiode, a beam splitter 05 and an electronic control system 06 with integrated computation unit. The electronic control system 06 is connected to the pulsed light source 03 and the light sensor 04 by means of leads 07 and 08.

At the beginning of the measurement, the electronic control system 06 generates an initial pulse so that the pulsed light source 03 delivers an initial light pulse 09$a$. This initial light pulse 09$a$ is reflected at the various tissue surfaces of the eye 02, in particular at the retina 10, and the reflection light pulse 11 is guided to the light sensor 04 after deflection at the beam splitter 05. Pulsed light source 03, beam splitter 05 and light sensor 04 are arranged in such a manner that the length of the ray path from the pulsed light source 03 to the retina 10 is precisely as long as the ray path from the retina 10 to the light sensor 04.

As soon as a reflection light pulse 11 is detected at the light sensor 04, this is passed on to the electronic control system 06 via the lead 08. After receiving this detection signal, the electronic control system 06 triggers another light pulse, namely a follow-up light pulse 09b, of the pulsed light source 03 via the lead 07. The follow-up light pulse 09b is again reflected at the retina 10 and detected as reflection light pulse 11 at the light sensor 04. Detection of the reflection light pulse 11 again triggers another follow-up pulse 09b.

Since the distance of the eye 02 to the device 01 substantially does not change, the resonant circuit formed from the pulsed light source 03, the retina 10, the light sensor 04 and the electronic control system 06 then oscillates at a particular frequency F1. This frequency F1 corresponds to the reciprocal of the propagation time required by the light to propagate from the pulsed light source 03 to the retina 10 and back from the retina 10 t the light sensor 04. The measured frequency F1 also includes the delay time required, depending on the component, to deliver the successive follow-up light pulse 09b at the pulsed light source from receipt of the reflection light pulse 11 at the light sensor 04. If this delay time is sufficiently short, or if the device 01 is suitably calibrated, the component-dependent delay time can be neglected or corrected.

Since the length of the ray path from the pulsed light source 03 to the retina and back from the retina to the light sensor 04 is the same, the formula X=0.5×c (specific velocity of light)×t (propagation time for an oscillation) is valid. The propagation time t for an oscillation can be replaced by the reciprocal of the measured frequency 1/F so that the distance X is calculated using the formula X=0.5×c×1/F1.

Figure 2:
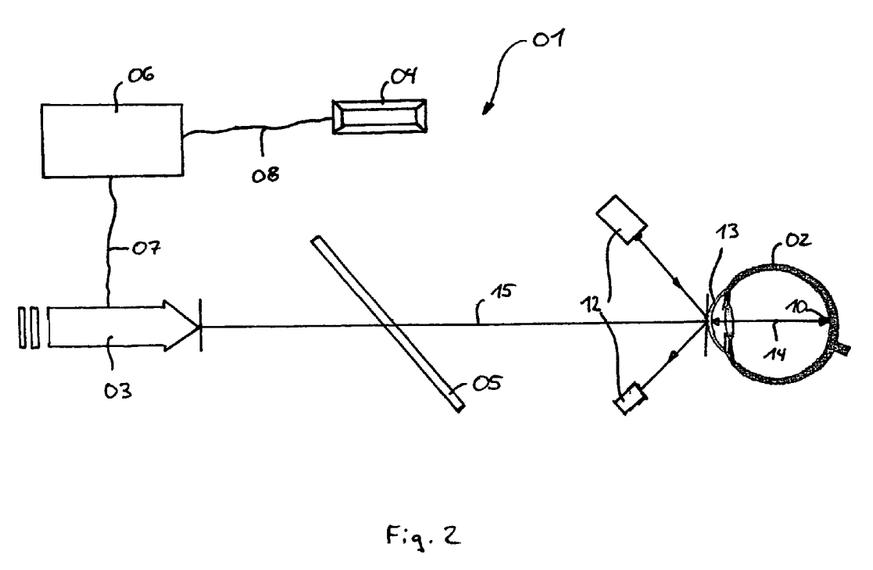
FIG. 2: shows the device according to FIG. 1 combined with an independent measuring device for measuring the distance from a measurement point on a second tissue surface on the outer side of the eye.

FIG. 2 shows how the distance X determined by the frequency measurement can be further used within the framework of an eye examination. If, according to the embodiment shown in FIG. 2, a second independent measuring device 12, namely a triangulation measuring device is integrated in the device 01, which can determine the distance of the anterior side of the cornea 13, the final result includes measurement results for the distance of the device 01 from the retina 10 and for the distance of the device 01 from the cornea 13 so that the axial length 14 of the eye can be determined by corresponding subtraction.

Figure 3:
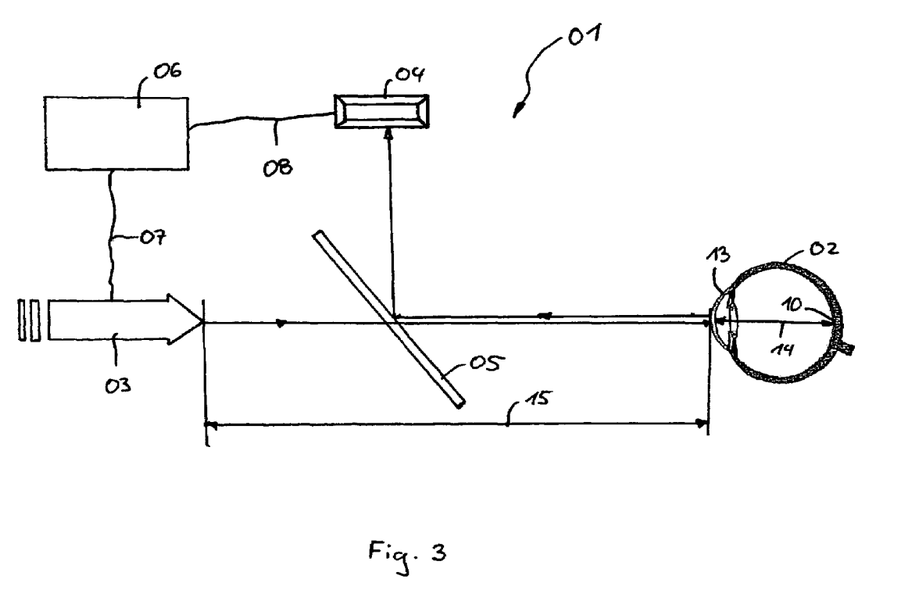
FIG. 3: shows the device according to FIG. 1 with a second ray path for measuring the distance from a second measurement point on a second tissue surface of the eye.

FIG. 3 illustrates an alternative method for determining the axial length 14. In this method, as in the procedure shown in FIG. 1, the distance x between pulsed light source 03 and retina 10 is first determined. Then as shown in FIG. 3, a resonant circuit is constructed from the pulsed light source 03, the cornea 13, the light sensor 04 and the electronic control system 06 and the resulting oscillation frequency F2 is measured. Without calculating the distance 15 between the pulsed light source 03 and the cornea 13, axial length 14 is derived as the length difference XD according to the formula XD=0.5×c (1/F2−1/F1). The measurement errors caused by the delay time of the components are easily eliminated by this measurement and calculation method since the corresponding measurement errors are each the same size in the measurement of the frequency F1 and in the frequency F2 and are therefore eliminated.

Figure 4:
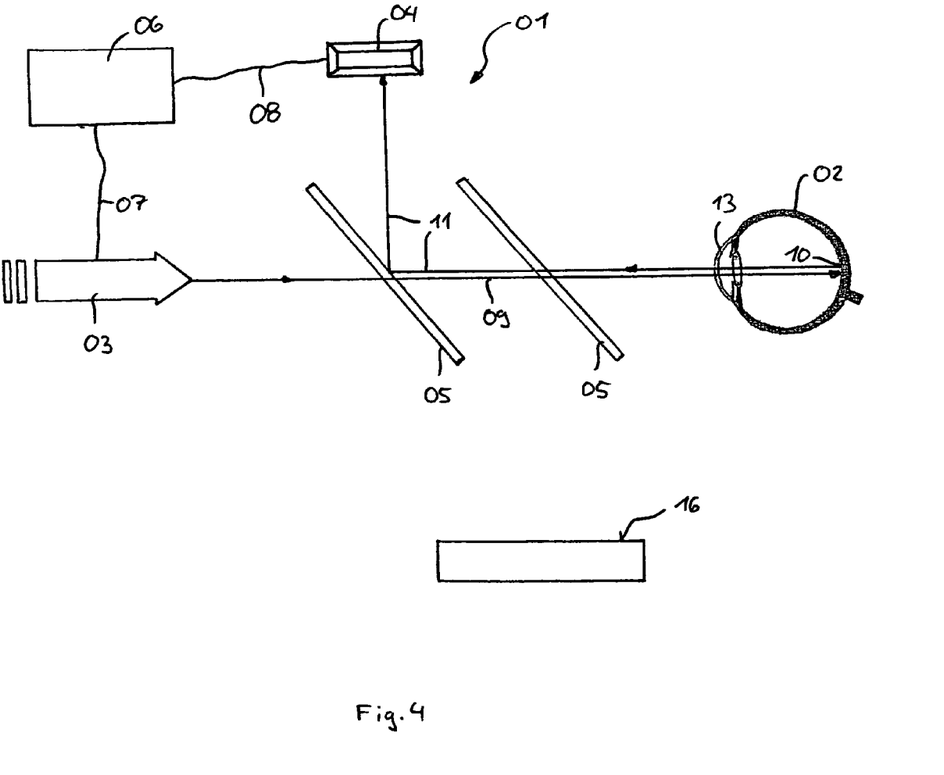
FIG. 4: shows a second embodiment of a device for measuring distances at the eye.
Figure 5:
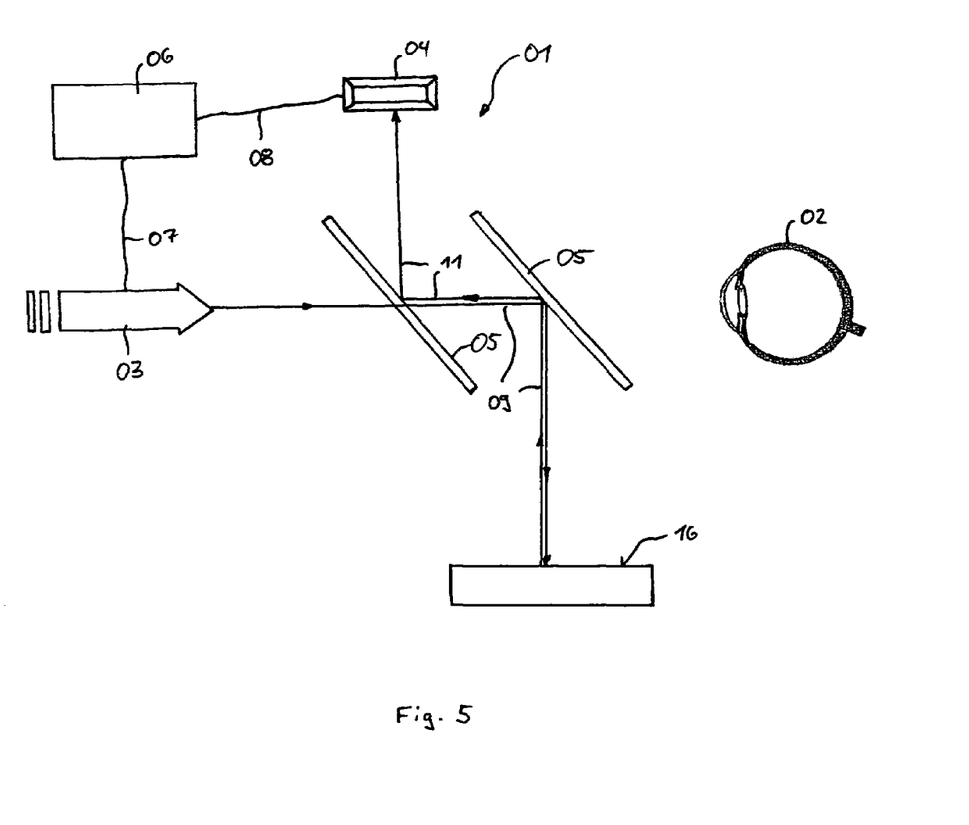
FIG. 5: shows the device according to FIG. 4 when measuring the distance from a measurement point on a reference surface.
Figure 6:
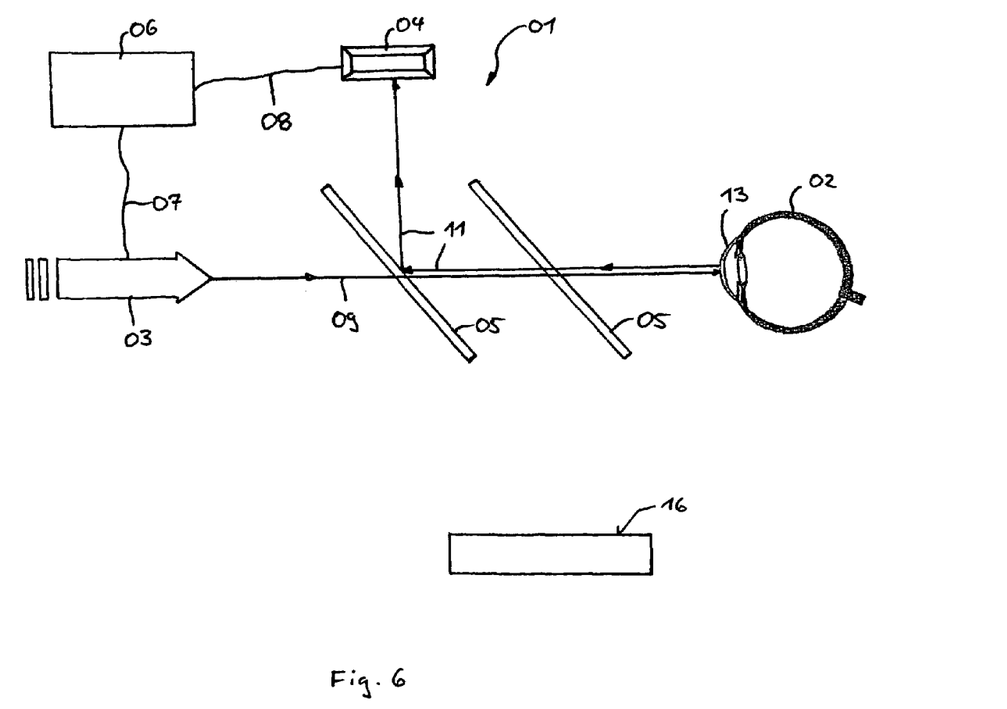
FIG. 6: shows the device according to FIG. 4 when measuring the distance from a second tissue surface of the eye.

FIGS. 4 to 6 show a second variant for eliminating the measurement error caused by the delay time of the components. In this variant, as shown initially in FIG. 4, a resonant circuit comprising a first tissue surface, in the example shown the retina 13 is again built up and the resulting oscillation frequency F1 is measured.

Then as shown in FIG. 5, a resonant circuit is built up in which the light is reflected at a reference surface 16 and the resulting oscillation frequency F2 is measured. The length difference XD which represents the different length of the two ray paths shown in FIG. 4 and FIG. 5 can then be derived from the two measured frequencies F1 and F2 using the formula XD=0.5×c×(1/F2−1/F1). The component-dependent delay times can again be eliminated since they are represented as the same size in both frequencies.

Similarly, as shown in FIG. 6, a resonant circuit is built up with a second tissue surface, in the example shown with the cornea 13 and the resulting oscillation frequency F3 is measured. The length difference XD2 between the ray path shown in FIG. 6 and the ray path shown in FIG. 5 during reflection at the reference surface 16 is again obtained from the formula XD2=0.5×c×(1/F2−1/F3). If XD1 is now subtracted from XD3, the axial length 14 is obtained directly.

Figure 7:
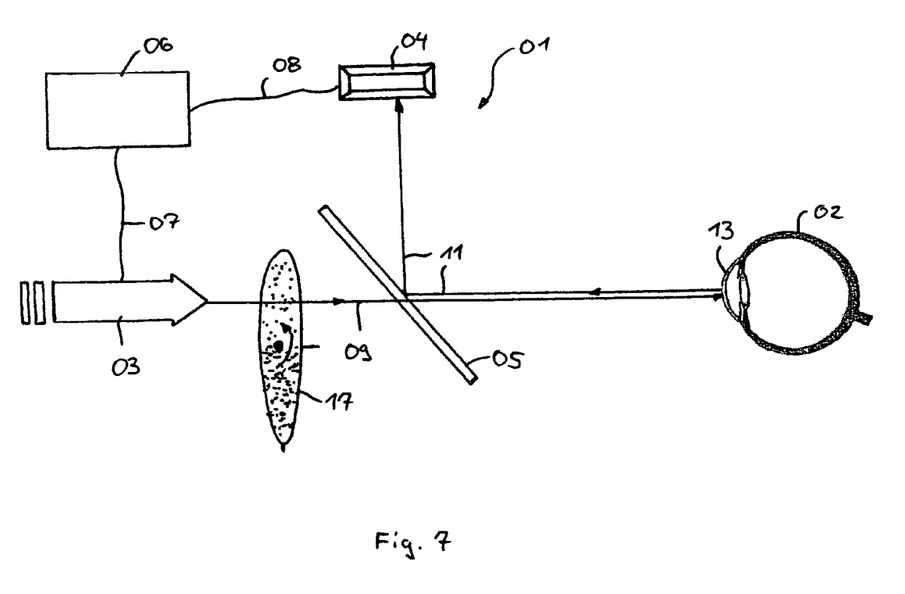
FIG. 7: shows the device according to FIG. 1 where a darkening device is additionally used.
Figure 8:
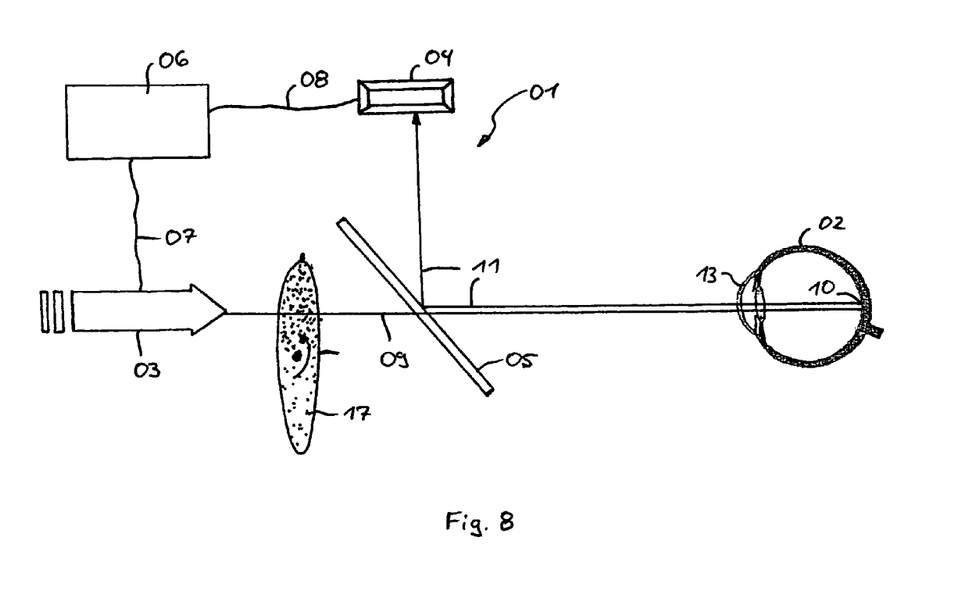
FIG. 8: shows the device according to FIG. 7 after shifting the darkening device.

FIGS. 7 to 8 show a schematic variant whereby the resonant circuits can be switched between the different tissue surfaces of the eye. In order to achieve this, a darkening device 17, namely a rotatably mounted optical wedge, is inserted in the ray path. By turning the optical wedge 17, the pulsed light 09 emitted by the pulsed light source 03 can be attenuated at different intensity. FIGS. 7 and 8 show the ray path schematically for different adjusting angles of the darkening device 17, the darkening being stronger in the situation shown in FIG. 8 than in the situation shown in FIG. 7.

Figure 9:
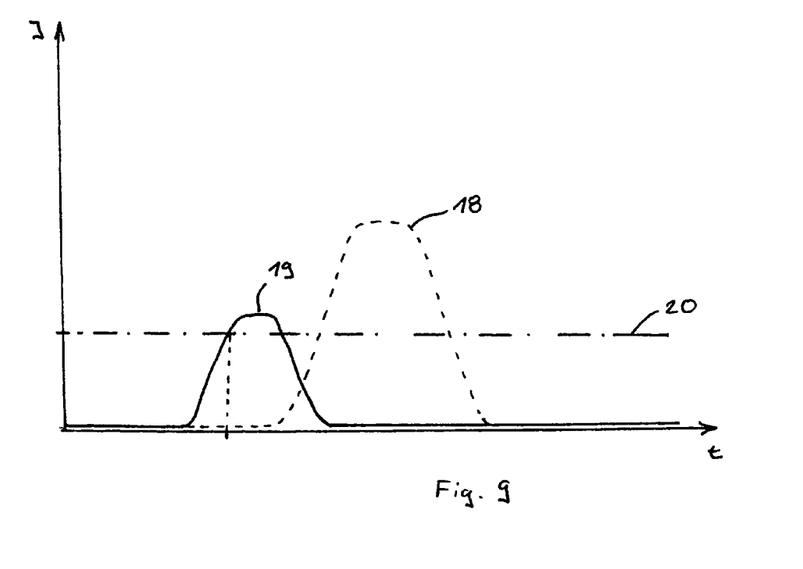
FIG. 9: shows the intensities of the reflector light pulses at three different tissue surfaces when adjusting the darkening device according to FIG. 7.

FIG. 9 schematically shows the intensities of the reflector light pulses reflected at the various tissue surfaces of the eye, which are received at the light sensor 04. The strongest reflection light pulse is produced by reflection at the retina 10 which is shown as the dashed reflection light curve 18 in FIG. 9. The reflection light curve 19 of the light reflected at the cornea has a weaker intensity and is located somewhat earlier in time than the maximum of the reflection light curve 18 because of the shorter distance of the cornea from the pulsed light source 03. A trigger threshold 20 is defined in the control device 06 for differentiating the reflection light between the two tissue surfaces, namely between the retina and the cornea. In other words, this means that the next follow-up light pulse of the pulsed light source 03 is always triggered by the control device 06 when the trigger threshold 20 is exceeded by the sensor signal. After triggering a follow-up light pulse the triggering of a next follow-up light pulse is eliminated for a certain time interval dependent on the components or by suitable measures. In the signal profile shown in FIG. 9, this means that as a result of the relatively low trigger threshold 20, the follow-up light pulse is triggered in each case by reflection light 19 from the cornea so that the resonant circuit shown in FIG. 7 is built up during reflection of the light pulse at the cornea 13. The reflection light 18 from the retina on the other hand is not taken into account as a result of the component-dependent dead time after triggering the respectively next follow-up light pulse.

Figure 10:
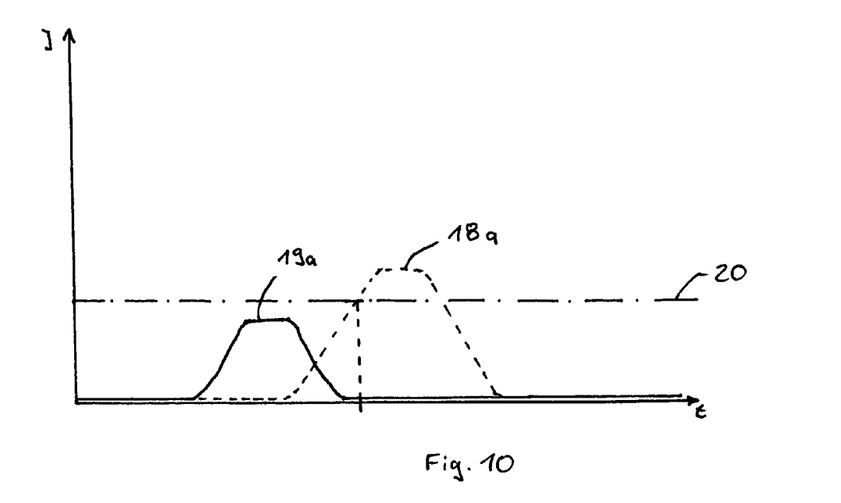
FIG. 10: shows the intensities of the reflector light pulses when adjusting the darkening device according to FIG. 8.

The intensities of the reflection light 18a and 19a shown in FIG. 10 correspond to the situation after darkening the ray path by turning the optical wedge 17. As a result of the lower light intensity of the light pulses incident on the retina 10 or on the cornea 13, the reflection light curves 18 and 19 are correspondingly lowered. The reflection light 19 of the light reflected at the cornea is no longer sufficient to exceed the trigger threshold 20 so that the resonant circuit shown in FIG. 8 is now built up during reflection of light at the retina 10.

Figure 11:
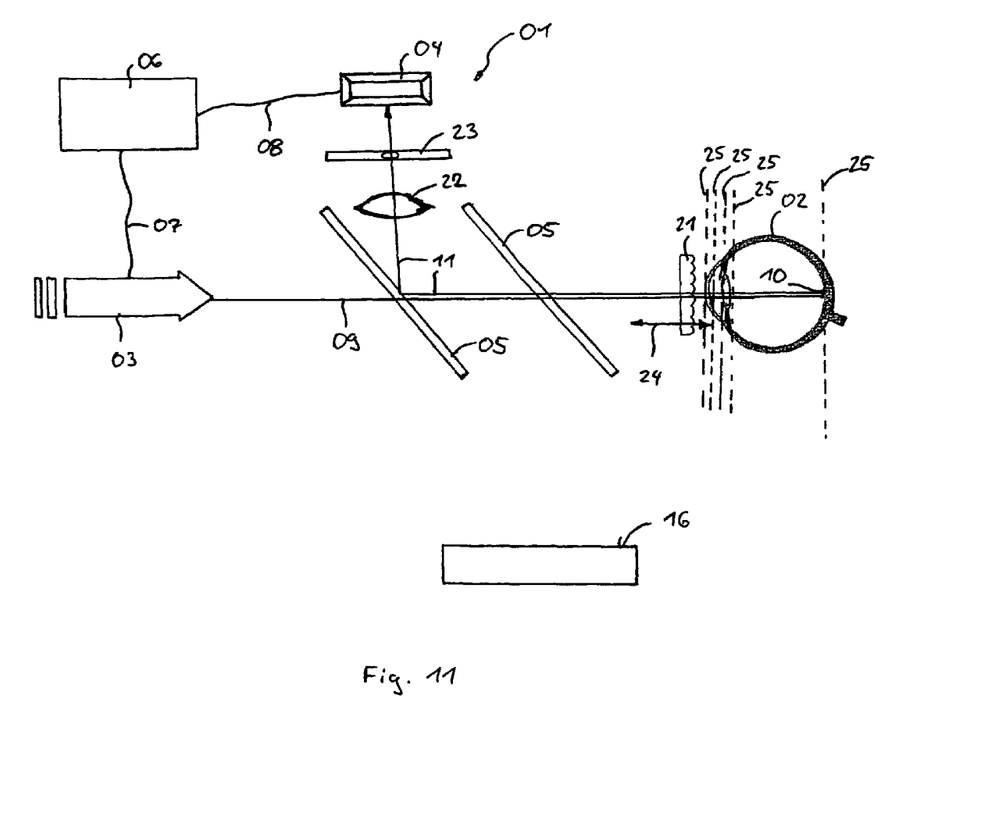
FIG. 11: shows a third embodiment of a device for measuring distances at the eye.

FIG. 11 shows an alternative to selecting the various tissue surfaces in the eye which are taken into account in the frequency measurement in each case. In this variant, a confocal optical filter is placed in the ray path of the reflection light, said filter consisting of a microlens array 21, a lens 22 and an aperture 23. Different measurement planes 25 in the eye can be focused by shifting the microlens array 21 according to the adjusting path 24 indicated. The additional arrangement 22 and the aperture 23 in the ray path of the reflection light ensure that in each case, only measurement planes focused by the microlens array are imaged on the light sensor 04 whereas all other regions of the eye 02 are masked out. During the measurement of the eye 02, the microlens array 21 can now be moved starting from an initial position slowly towards the eye from the front or moved away from the eye so that the measurement plane 25 is thereby displaced continuously through the eye 02. Whenever one of the tissue surfaces in the eye at which the pulsed light is reflected, is focused with the microlenses of the array 21, that is when the measurement plane 25 runs through the corresponding tissue surface, the reflection light pulse reflected in this tissue surface is transmitted to the light sensor 04. All other reflection light pulses reflected at other tissue surfaces are filtered out by the aperture 23. As soon as a reflection light pulse is detected at the light sensor 24, a resonant circuit is built up and the corresponding oscillation frequency is measured. As soon as the oscillation frequency is determined, the microlens array 21 is shifted further and the pulsed light source 03 emits follow-up light pulses at regular intervals in quick succession until a reflection light pulse is again received and another resonant circuit is built up again.

The various distances between the individual tissue surfaces 02 can be derived from the successively determined oscillation frequencies F1 to Fn.

REFERENCE LIST

01 Device
02 Eye
03 Pulsed light source
04 Light sensor
05 Beam splitter
06 Electronic control system
07 Lead
08 Lead
09 Light pulse
10 Retina
11 Reflection light pulse
12 Triangulation measuring device
13 Cornea
14 Axial length of the eye
15 Distance between pulsed light source and cornea
16 Reflecting reference surface
17 Darkening device
18 Reflection light curve (retina)
19 Reflection light curve (cornea)
20 Trigger threshold
21 Microlens array
22 Lens
23 Aperture
24 Adjusting distance
25 Measurement plane (optical filter)

What is claimed is:

1. A method for determining the distance from a measurement point on a tissue surface (10, 13) of the eye (02), comprising:

a) an initial light pulse (09a) is generated using a pulse light source (03) and is directed onto the measurement point of the eye, b) a reflector light pulse (11) reflected on the tissue surface (10, 13) at the measurement point is intercepted by a light sensor (04), c) a followup light pulse (09b) of the pulsed light source (03) is triggered by the detection of the reflector light pulse (11) at the light sensor (04), d) the pulsed light source (03) generates further follow-up light pulses (09b) depending on the detection of the reflector light pulses (11) caused by the respectively preceding follow-up light pulses (09b) and thereby oscillates at a frequency F1, e) the frequency F1 is measured directly or indirectly, f) the length X of the ray path starting from the pulsed light source (03) via the measurement point to the light sensor (04) is derived from the measured value F1 and the specific speed of light c at which the light propagates in the medium along the ray path.

2. The method according to claim 1, wherein the length X of the ray path is deduced in accordance with the formula $$X=0.5 \times c \times (1/F1).$$

3. The method according to claim 1, wherein the frequency F1 at which the pulsed light source (03) oscillates during reflection of the light pulses (09) at a first measurement point on tissue surfaces (10, 13) of the eye is measured, a frequency F2 at which the pulsed light source (03) oscillates during reflection of the light pulses (09) at a second measurement point is measured, and the length difference XD by which the lengths X1 and X2 of the two ray paths differ during reflection of the light pulses (09) at the first measurement point and during reflection of the light pulses (09) at the second measurement point is derived from the measured values of F1, F2 and the specific speed of light c.

4. The method according to claim 3, wherein the length difference XD between the two ray paths is derived according to the formula $$XD=0.5 \times c \times (1/F2-1/F1).$$

5. The method according to claim 3, wherein the second measurement point lies on a second tissue surface (10, 13) of the eye (02), wherein the length distance XD represents the difference between the two tissue surfaces (10, 13), in particular between the retina (10) and the cornea (13).

6. The method according to claim 3, wherein the second measurement point lies on a reflecting reference surface (16), wherein the length difference XD represents the different length of the two ray paths during reflection of the light pulses (09) at the first measurement point on one tissue surface (10, 13) of the eye (02) and during reflection of the light pulses (09) at the second measurement point on the reflecting reference surface (16).

7. The method according to claim 6, wherein the second measurement point is disposed on the reflecting reference surfaces (16) in a defined position, in particular in a defined position relative to a reference point.

8. The method according to claim 1, wherein a second independent measurement method is used to determine the distance between a reference point and a measurement point on a tissue surface on the outer side of the eye, in particular on the anterior side of the cornea (13).

9. The method according to claim 8, wherein the distance determined using the second independent measurement method is used to pre-set and/or monitor the frequency measurement method.

10. The method according to claim 8, wherein the distance between the reference point and a reflecting measurement point on a tissue surface in the interior of the eye (02), on particular on the retina (10) is determined using the frequency measurement method, wherein the distance which exists between a tissue surface (10) in the interior of the eye (02) and a tissue surface (13) on the outer side of the eye (02) is derived by subtracting the distance determined using the second independent measurement method from the distance determined using the frequency measurement method.

11. The method according to claim 6, wherein
a length difference XD1 which represents the different length of the two ray paths during reflection of the light pulses (09) at the first measurement point on a first tissue surface (10) of the eye (02) and during reflection of the light pulses (09) at the second measurement point on a reflecting reference surface (16) is determined,
a length difference XD2 which represents the different length of the two ray paths during reflection of the light pulses (09) at a third measurement point on a second tissue surface (13) of the eye (02) and during reflection of the light pulses (09) at the second measurement point on a reflecting reference surface (16) is determined,
the distance between the first measurement point on the first tissue surface (10) of the eye (02) and the third measurement point on a second tissue surface (13) of the eye (02) is derived from the difference between XD1 and XD2.

12. The method according to claim 1, wherein the reflector light pulse (11) is detected at the light sensor (04) by the light intensity measured by the light sensor (04) exceeding and/or falling below at least one predetermined trigger threshold (20).

13. The method according to claim 12, wherein the frequency measurement method is repeated in at least two measurement runs, wherein the light intensity of the light pulses (09) is varied between the different measurement runs.

14. The method according to claim 13, wherein the light intensity is varied by inserting a darkening element (17), in particular by displacing an optical wedge element in the ray path of the light pulses (09).

15. The method according to claim 1, wherein during the frequency measurement to determine the frequency F, the measurement duration is measured using a time measuring device and the light pulses (09) delivered during the measurement duration are counted using a pulse counting member.

16. The method according to claim 1, wherein during the frequency measurement to determine the frequency F, the measurement duration is predefined as a fixed value and the light pulses (09) delivered during the fixed measurement duration are counted using the pulse counting member.

17. The method according to claim 1, wherein during the frequency measurement to determine the frequency F, the frequency of the light pulses (09) to be delivered is predefined as a fixed value and the measurement duration required to deliver the light pulses (09) predefined as a fixed value is measured using the time measuring device.

18. The method according to claim 1, wherein a confocal optical filter (21, 22, 23) is disposed in the ray path of the reflector light pulses (11), wherein the optical filter (21, 22, 23) transmits reflector light pulses (11) reflected in the near-field range of a specific measurement plane (25) of the optical filter and filters out reflector light pulses (11) reflected outside the near-field range of the measurement plane (25).

19. The method according to claim 18, wherein the optical filter (21, 22, 23) is shifted continuously or in steps in such a manner that, starting from an initial position, the measurement plane (25) is shifted along the longitudinal axis of the ray path as far as an end position, wherein a frequency measurement is carried out to determine the distance of the reflecting tissue surface when detecting reflector light pulses (11).

20. The method according to claim 19, wherein the initial position or end position of the measurement plane lies before or on the anterior side of the cornea (13).

21. The method according to claim 19, wherein the initial position or end position of the measurement plane lies before or behind the retina (10).

22. The method according to claim 1, wherein the position of the eye is fixed by operation of a fixing light source.

23. The method according to claim 1, wherein a flat height profile of the tissue surface is derived by measuring the distance of a plurality of adjacent measurement points on a tissue surface (10, 13) of the eye (02).

24. The method according to claim 23, wherein the distance of the plurality of adjacent measurement points on a tissue surface of the eye is measured by scanning the tissue surface, wherein a focused pulsed light beam is successively directed onto adjacent measurement points during the scanning.

25. The method according to claim 23, wherein in order to measure the distance of the plurality of adjacent measurement points on a tissue surface of the eye, a flat pulsed light beam is directed onto the tissue surface, wherein the pulsed light beams reflected at individual measurement points are detected separately from one another by a flat light sensor, in particular a flat CCD chip sensor.

26. The method according to claim 23, wherein a flat height profile of the nerve fibre head is derived at the end of the optic nerve.

27. The method according to claim 23, wherein a flat height profile of the cones on the retina is derived.

28. The method according to claim 1, wherein at least one reflecting measurement point on a tissue surface lies on the outer side of the eye (02), in particular on the anterior side of the cornea (13).

29. The method according to claim 1, wherein at least one reflecting measurement point on a tissue surface lies in the interior of the eye (02).

30. The method according to claim 29, wherein one measurement point lies on the retina (10).

31. The method according to claim 29, wherein one measurement point lies on the posterior side of the cornea (13) and/or on the anterior side of the lens body and/or on the posterior side of the lens body.

32. The method according to claim 1, wherein the distance between one measurement point on the anterior side of the cornea (13) and one measurement point on the retina (10) is determined and is output as the axial length (14) of the eye (02).

33. The method according to claim 1, wherein an averaged speed, averaged from the propagation velocity of light in the various media along the ray path between the pulsed light source (03) and the measurement point, is used as the specific speed of light c.

34. The method according to claim 1, wherein the specific speed of light c is averaged from the propagation velocity of light in air and the averaged propagation velocity of light in the eye (02).

35. The method according to claim 1, wherein the averaged propagation velocity of light in the eye (02) is averaged from the propagation velocity in the various media of the eye (02), in particular in the cornea (13) and/or in the anterior chamber and/or in the lens tissue and/or in the aqueous humor.

36. A device for determining the distance from a measurement point on a tissue surface (10, 13) of the eye (02), comprising:

at least one pulsed light source (03) for generating light pulses (09) which can be directed onto the measurement point, and at least one light sensor (04) for detecting reflector light pulses (11) reflected at the measurement point, and an electronic control system (06) which triggers further followup light pulses (09b) after detecting a reflector light pulse (11) and at the same time oscillates at a frequency F1, and a frequency measuring device for direct or indirect measurement of the frequency F1, an a computation unit whereby the length X of the ray path starting from the pulsed light source (03) via the measurement point on the tissue surface (10, 13) of the eye (02) to the light sensor (04) is derived from the measured value F1 and the specific speed of light c at which the light propagates in the medium along the ray path.

37. The device according to claim 36, wherein the pulsed light source (03) and the light sensor (04) are arranged in the device (01) in such a manner that the length X of the ray path between the pulsed light source (03) and the measurement point exactly corresponds to the length Y of the ray path between the measurement point and the light sensor (04).

38. The device according to claim 36, wherein the pulsed light source (03) is embodied in the manner of a laser light source, in particular in the manner of a laser diode.

39. The device according to claim 36, wherein the light sensor (04) is embodied in the manner of a photodiode or in the manner of an in particular, flat CCD chip sensor.

40. The device according to claim 36, wherein the device (01) comprises a reflecting reference surface (16) with a second measurement point located thereon, wherein light pulses (09) are directed onto the second measurement point and can be reflected therefrom as reflection light pulses (11).

41. The device according to claim 40, wherein the second measurement point is disposed on the reflecting reference surfaces (16) in a defined position, in particular in a defined position relative to a reference point.

42. The device according to claim 36, wherein a second independent measuring device (12) is integrated in the device (01), whereby the distance between a reference point and a measurement point on a tissue surface on the outer side of the eye, in particular on the anterior side of the cornea, can be determined.

43. The device according to claim 42, wherein the second independent measuring device (12) is embodied in the manner of a triangulation measuring device.

44. The device according to claim 36, wherein the light intensity of the light sensor (04) is evaluated in a light intensity trigger element, wherein the reflector light pulse (11) is detected at the light sensor (04) by the fact that the light intensity measured by the light sensor exceeds or falls below a predefined trigger threshold (20).

45. The device according to claim 36, wherein the device (01) comprises a darkening element (17), in particular an optical wedge element whereby the light intensity of the light pulses (09) can be varied.

46. The device according to claim 36, wherein for measuring the frequency when determining the frequency F, a time measuring device and/or a pulse counting member is provided for counting the pulses delivered by the pulsed light source.

47. The device according to claim 46, wherein the pulse counting member is preceded by a divider element which divides the number of light pulses delivered by the pulsed light source in a fixedly predefined ratio and passes on the divider result for evaluation.

48. The device according to claim 36, wherein a storage element is provided in the device, in which the measurement duration during the frequency measurement and/or the light pulses (09) to be delivered in the frequency measurement can be stored as a fixed value.

49. The device according to claim 36, wherein the device comprises a confocal optical filter (21, 22, 23) which can be inserted in the ray path of the reflector light pulses (11), wherein the optical filter (21, 22, 23) transmits reflector light pulses (11) reflected in the near-field range of a specific measurement plane (25) and wherein said optical filter (21, 22, 23) filters out reflector light pulses (11) reflected outside the near-field range of said measurement plane (25).

50. The device according to claim 49, wherein the confocal optical filter (21, 22, 23) comprises a lens system (21, 22) for focusing the measurement points located in the measurement plane (25) and an aperture (23) for filtering out all non-focused reflector light pulses (11).

51. The device according to claim 49 wherein the lens system (21, 22) for focusing the measurement points located on the measurement plane (25) comprises a microlens element (21) provided with a plurality of microlenses disposed in one plane.

52. The device according to claim 49, wherein at least one lens (22) of the optical filter is adjustably mounted to adjust the measurement plane (25) of the confocal optical filter (21, 22, 23).

53. The device according to claim 36, wherein the device (01) comprises a fixing light source.

* * * * *